US006630139B2

(12) United States Patent
Chiou

(10) Patent No.: US 6,630,139 B2
(45) Date of Patent: Oct. 7, 2003

(54) FIBRINOGENOLYTIC PROTEASES WITH THROMBOLYTIC AND ANTIHYPERTENSIVE ACTIVITIES: MEDICAL APPLICATION AND NOVEL PROCESS OF EXPRESSION AND PRODUCTION

(75) Inventor: Shyh-Horng Chiou, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/939,126

(22) Filed: Aug. 24, 2001

(65) Prior Publication Data

US 2003/0039644 A1 Feb. 27, 2003

(51) Int. Cl.$^7$ .......................... A61K 38/00; C12N 9/48; C12N 9/64; C07K 17/00; C07K 1/00

(52) U.S. Cl. .................... 424/96.64; 435/212; 435/226; 530/412; 530/416; 530/417; 530/856; 514/2

(58) Field of Search ................................ 435/212, 226; 514/2; 424/94.64; 530/412, 856, 416, 417

(56) References Cited

U.S. PATENT DOCUMENTS

| 3,713,981 A | * | 1/1973 | Broadbent .................... 195/62 |
| 4,568,545 A | * | 2/1986 | Mihara et al. ................. 424/94 |
| 2001/0009774 A1 | * | 2/2001 | Kapeller-Libermann ... 435/69.1 |
| 2002/0064856 A1 | * | 5/2002 | Plowman .................... 435/226 |

OTHER PUBLICATIONS

Stocker, K Defibrinogenation with thrombin–like snake venom enzymes (1978) in Handbook of Experimental Pharmacology (Markwardt, F., Ed.), vol. 46, pp. 451–484, Springer–Verlag.*
Steadman Steadman's Medical Dictionary 26$^{th}$ Ed (1995).*
Hung CC, Chiou SH. Fibrinogenolytic proteases isolated from the snake venom of Taiwan habu: serine proteases with kallikrein–like and angiotensin–degrading activities. Biochem biophys Res Commun. Mar. 9, 2001;281.*
Yamaguchi T, Carretero OA, Scicli AG. A novel serine protease with vasoconstrictor activity coded by the kallikrein gene S3. J Biol Chem. Mar. 15 1991;266(8):5011–7.*
Lottenberg, R., et al., Assay of coagulation proteases using peptide chromogenic and fluorgenic substrates. In: Meth. Enzymol. v80, p341–361 (1981).*
Bakker WW et al, The glomerular polyanion of the rat kidney III. Br J Exp Pathol 1984 66(1) p47–56.*
Garrett JR et al, Use of different derivatives of D–Val–Leu–Arg for studying kallikrein activities in cat submandibular glands and saliva. Histochem. J. (1985) v 17(7) p 805–18.*
Guyton and Hall (1996) Cardiac Failure Chapter 22 p266.2 and p206.4.1–2 In: Textbook medical physiology W.B Sauders Co Philadelphia, PA.*

Chin–Chun Hung et al, "Characterization of One Novel Venome Protease with β–Fibrinogenase Activity from the Taiwan Habu (Trimeresurus Mucrosquamatus): Purification and cDNA Sequence Analysis", Biochemical and Biophysical Research Communications, pp. 1707–1715, vol. 205, No. 3, 1994.
F. S. Markland, "Snake Venoms and the Hemostatic System", Toxicom, vol. 36, No. 12, pp 1749–1800, 1998.
Shyh–Horng Chiou, "The Evaluation of the Temperature Effect and Hydrolysis Conditions for Amino Acid Analysis", Biochemistry International, vo. 17, No. 5, pp. 981–987, Nov., 1988.
Shyh–Horng Chiou, Characterization of a Protease with –and β– Fibrinogenase Activity from the Western Diamondback Rattlesnake, *Crotalus Atrox*, Biochemical and Biophysical Research Communications, vol. 187, No. 1, pp. 389–396, 1992.
Solange M. T. Serrano, Purification, Characterization, and Amino Acid Sequence of a Serine Proteinase, PA–BJ, with Platelet–Aggregating Activity from the Venom of *Biothrops jararaca*, Biochemistry, vol. 34, No. 21, pp. 7186–7193, 1995.
Shyh–Horng Chiou, Isolation of a Crotalase–Like Protease with –Fibrinogenase Activity from the Western Diamondback Rattlesnake, *Crotalus Atrox*, Biochemistry International, vol. 26, No. 1, pp. 105–112, Feb. 1992.
J. B. Bjarnason et al., "Kallikrein–like Enzymes from *Crotalus atrox* Venom", The Journal of Biochemical Chemistry, vol. 258, No. 20, Oct. 25, pp. 12566–12573, 1983.
M. C. Smith, "Chelating Peptide–immobilized Metal Ion Affinity Chromatography", The Journal of Biological Chemistry, vol. 263, No. 15, Issue of May 25, pp. 7211–7215, 1988.
M. Maeda, et al., "Expression of cDNA for Batroxobin, a Trobin–Like Snake Venom Enzyme", J. Biochem., vol. 109, No. 4, pp. 632–637 (1991).
U. K. Laemmli, "Cleavage of Structural Proteins During the Assembly of the head of Bacteriophase T4", Nature, vol. 227, pp. 680–685, (1970).
W. H. Holleman et al., "The Thrombin–like Enzyme from *Bothrops atrox* Snake Venom", The Journal of Biological Chemistry, vol. 251, No. 6, pp. 1663–1669, (1976).
J. Porath et al., "Metal Chelate Affinity Chromatography, a New Approach to Protein Fractionation", Nature, vol. 258, pp. 598–599 (1975).
F. S. Markland et al, Purification and Properties of a Thrombin–like Enzyme from the Venom of *Crotalus adamanteus* (Eastern Daimondback Rattlesnake), The Journal of Biological Chemistry, vol. 216, No. 21, pp. 6160–6173, 1974.

(List continued on next page.)

Primary Examiner—Rebecca E. Prouty
Assistant Examiner—Sheridan L. Swope
(74) Attorney, Agent, or Firm—Cohen, Pontani, Lieberman & Pavane

(57) ABSTRACT

The present invention provides a process of producing highly purified proteases. The invention further provides the use of such purified proteases in treating cardiovascular disorders, including hypertension, stroke and thrombosis.

7 Claims, 12 Drawing Sheets

OTHER PUBLICATIONS

B. V. Pandya et al., "Anticoagulant Proteases from Western Diamondback Rattlesnake (*Crotalus atrox*) Venom", The Journal of Biochemistry, 1984, 23, pp. 460–470.

M. R. Ewart et al., "The Proteolytic Action of Arvin on Human Fibronogen", Journal of Biochemistry, (1970) 119, pp. 603–609. Apr. 11, 2003.

Bjarnason et al, Hemorrhagic Toxins from Western Diamondback Rattlesnake (*Crotalus atrox*) Venom: Isolation and Characterization of Five Toxins and the Role of Zinc in Hemorrhagic Toxin e, 3395–1404.

C. Ouyang et al., "Fibrinogenolytic Enzymes of *Trimeresurus Mucrosquamatus* Venom", Biochimica et Biphysica Acta, 420 (1976) pp. 309–315.

H. Pan et al., "cDNA Closing and Expression of Acutin, a Thrombin–Like Enzyme from *Agkistrodon acutua*", Biochemical and Biophysical Research Communications, 255, 412–415 (1999).

L. Au et al., "Molecular Cloning and Sequence Analysis of the cDNA for Ancrod, a Thrombin–Like Enzyme from the Venom of *Calloselasma Rhodostoma*", Biochemical Journal (1993), 294, 387–390.

N. Itoh, "Molecular Cloning and Sequence Analysis of cDNA for Batroxobin, a Thrombin–Like Snake Venom Enzyme", The Journal of Biological Chemistry, vol. 262, (1987), No. 7, pp. 3132–3135.

J. A. Rosenthal, "The Functional Role of Positively Charged Amino Acid Side Chains in –Bungarotoxin Revealed by Site–Directed Mutagenesis of His–Tagged Recombinant –Bungarotoxin", Biochemistry, 1999, 38, pp. 7847–7855.

W. Lin, "Species Difference in Circulatory and Respiratory Effects of Endothelin–1 and Sarafotoxin $S_{6b}$", Asia Pacific Journal of Pharmacology 1991, pp. 277–286.

K. F. Huang et al. , Characterization of Three Fibrinogenolytic Proteases Isolated from the Venome of Taiwan Habu (*trimeresurus mucrosquamatus*), Biochemistry Biology International, vol. 31, No. 6, Dec. 1993.

M. Uhlén et al., "Gener Fusions for Purpose of Expression: An Introduction", Methods in Enzymology, vol. 185, pp. 129–143.

F. Fiedler et al., "Separation of Kinins by High–Performance Liquid Chromatography", Methods in Enzymology, vol. 163, pp. 257–262.

R. M. Kini eat al., "Effects of Snake Venom Proteins on Blood Platelets", Toxicom, vol. 28, No. 12, pp. 1387–1422, 1990.

J. A. Rosenthal, "Functional Expression and Site–Directed Mutagenesis of a Synthetic Gene for –Bungarotoxin", The Journal of Biological Chemistry, vol. 269, No. 15, Apr. 1994, pp. 11178–11185.

Y. Zhang, "Trimeresurus *stejnegeri* Snake Venom Plasminogen Activator", The Journal of Biological Chemistry, vol. 272, No. 33, Aug. 1997, pp. 20531–20537 1976 Apr. 11, 2003.

A. M. Moura–da–Silva, et al., "Jarahagin ECD–Containing Disintegrin Domain: Expression in *Escherichia coli* and Inhibition of the Platelet–Collagen Interaction", Archives of Biochemistry and Biophysics, vol. 369, No. 2, Sep. 1999, pp. 295–301.

F. S. Markland, Jr., Snake Venom Fibrinogenolytic and Fibrinolytic Enzymes: An Updated Inventory, Thromb Haemost 1998; 79–668–74.

H. Pirkle, "Thrombin–like Enzymes from Snake Venoms: An Updated Inventory", Thromb Haemost 1998; 79: 675–83.

P. J. Gaffney et al., "Collaborative Study of a Proposed International Standard for Plasma Fibrinogen Measurement", Thrombosis and Haemostasis, pp. 428–432 (1992).

W. Burkhart et al., Amino Acid Sequence Determination of Ancrod, the Thrombin–like –fibrinogenase from the Venom of *Akistrodon rhodostoma*, FEBS Letters, vol. 297, No. 3, 297–301, Feb. 1992.

S. Kung et al., "Human Factor IX Corrects the Bleeding Diathesis of Mice with Hemophilia B", Blood, No. 91, No. 3, (Feb. 1998), pp. 784–790.

W. M. Holleman et al., "The Thrombin–like Enzyme from *Bothrops atrox* Snake Venom", The Journal of Biological Chemistry, 251, No. 6, pp. 1663–1669.

J. B. Bjarnason et al., "Hemorrhagic Toxins from Western Diamondback Rattlesnake (*Crotalus atrox*) Venom: Isolation and Characterization of Five Toxins and the Role of Zince in Hemorrhagic Toxin e", Characterization of Hemorrhagic Toxins, vol. 17, No. 16, 1978, pp. 3395–3404.

* cited by examiner

```
1  ATG AGA GGA TCG CAT CAC CAT CAC CAT CAC GGA TCC GAT GAC GAT GAC AAA GTC ATT GGA GGT GAT GAA
   Met Arg Gly Ser His His His His His His Gly Ser Asp Asp Asp Asp Lys Val Ile Gly Gly Asp Glu

2  ATG AGA GGA TCG CAT CAC CAT CAC CAT CAC GGA TCC TTC CTG CGT GTC ATT GGA GGT GAT GAA
   Met Arg Gly Ser His His His His His His Gly Ser Phe Leu Arg Val Ile Gly Gly Asp Glu

3  ------------------------------------------------TTC GTC CGT------------------------
                                                   Phe Val Arg

4  ------------------------------------------------TTC CCG CGT------------------------
                                                   Phe Pro Arg

5  ------------------------------------------------CCG TTC CGT------------------------
                                                   Pro Phe Arg

6  ------------------------------------------------CTG TTC CGT------------------------
                                                   Leu Phe Arg
```

FIGURE 1

SEQUENCE LISTING

```
<160> NUMBER OF SEQ ID NOS: 18

<210> SEQ ID NO 1
<211> LENGTH: 69
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(69)

<400> SEQUENCE: 1 atg aga gga tcg cat cac cat cac cat cac gga tcc gat gac gat gac        48
Met Arg Gly Ser His His His His His His Gly Ser Asp Asp Asp Asp
  1               5                  10                  15 aaa gtc att gga ggt gat gaa                                            69
Lys Val Ile Gly Gly Asp Glu
             20
```

<210> SEQ ID NO 2
<211> LENGTH: 63
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(63)

<400> SEQUENCE: 2

```
atg aga gga tcg cat cac cat cac cat cac gga tcc ttc ctg cgt gtc      48
Met Arg Gly Ser His His His His His His Gly Ser Phe Leu Arg Val
 1               5                  10                  15 att gga ggt gat gaa                                                  63
Ile Gly Gly Asp Glu
            20
```

<210> SEQ ID NO 3
<211> LENGTH: 63
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(63)

<400> SEQUENCE: 3

```
atg aga gga tcg cat cac cat cac cat cac gga tcc ttc gtc cgt gtc      48
Met Arg Gly Ser His His His His His His Gly Ser Phe Val Arg Val
 1               5                  10                  15 att gga ggt gat gaa                                                  63
Ile Gly Gly Asp Glu
            20
```

<210> SEQ ID NO 4
<211> LENGTH: 63
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(63)

<400> SEQUENCE: 4

```
atg aga gga tcg cat cac cat cac cat cac gga tcc ttc ccg cgt gtc      48
Met Arg Gly Ser His His His His His His Gly Ser Phe Pro Arg Val
 1               5                  10                  15 att gga ggt gat gaa                                                  63
Ile Gly Gly Asp Glu
            20
```

<210> SEQ ID NO 5
<211> LENGTH: 63
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(63)

<400> SEQUENCE: 5

```
atg aga gga tcg cat cac cat cac cat cac gga tcc ccg ttc cgt gtc      48
Met Arg Gly Ser His His His His His His Gly Ser Pro Phe Arg Val
```

```
            1               5                  10                 15
att gga ggt gat gaa                                                            63
Ile Gly Gly Asp Glu
         20

<210> SEQ ID NO 6
<211> LENGTH: 63
<212> TYPE: DNA
<213> ORGANISM: Unknown Organism
<220> FEATURE:
<223> OTHER INFORMATION: Description of Unknown Organism: Venom gene
      construct
<221> NAME/KEY: CDS
<222> LOCATION: (1)..(63)

<400> SEQUENCE: 6 atg aga gga tcg cat cac cat cac cat cac gga tcc ctg ttc cgt gtc     48
Met Arg Gly Ser His His His His His His Gly Ser Leu Phe Arg Val
 1               5                  10                 15
att gga ggt gat gaa                                                  63
Ile Gly Gly Asp Glu
         20

<210> SEQ ID NO 7
<211> LENGTH: 23
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 7

Met Arg Gly Ser His His His His His His Gly Ser Asp Asp Asp Asp
 1               5                  10                 15

Lys Val Ile Gly Gly Asp Glu
             20

<210> SEQ ID NO 8
<211> LENGTH: 21
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 8

Met Arg Gly Ser His His His His His His Gly Ser Phe Leu Arg Val
 1               5                  10                 15

Ile Gly Gly Asp Glu
         20

<210> SEQ ID NO 9
<211> LENGTH: 21
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 9

Met Arg Gly Ser His His His His His His Gly Ser Phe Val Arg Val
 1               5                  10                 15

Ile Gly Gly Asp Glu
         20
```

```
<210> SEQ ID NO 10
<211> LENGTH: 21
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 10

Met Arg Gly Ser His His His His His His Gly Ser Phe Pro Arg Val
 1               5                  10                  15

Ile Gly Gly Asp Glu
            20

<210> SEQ ID NO 11
<211> LENGTH: 21
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 11

Met Arg Gly Ser His His His His His His Gly Ser Pro Phe Arg Val
 1               5                  10                  15

Ile Gly Gly Asp Glu
            20

<210> SEQ ID NO 12
<211> LENGTH: 21
<212> TYPE: PRT
<213> ORGANISM: Unknown Organism
<220> FEATURE:
<223> OTHER INFORMATION: Description of Unknown Organism: Venom amino
      acid sequence

<400> SEQUENCE: 12

Met Arg Gly Ser His His His His His His Gly Ser Leu Phe Arg Val
 1               5                  10                  15

Ile Gly Gly Asp Glu
            20

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcggatccga tgacgatgac aaagtcattg gaggtgatg                               39

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (9)..(17)
<223> OTHER INFORMATION: Autolytic recognition site

<400> SEQUENCE: 14
gcggatccnn nnnnnnngtc attggaggtg atg                                     33
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcctgcagtc acaggggca ggttac                                            26

<210> SEQ ID NO 16
<211> LENGTH: 4
<212> TYPE: PRT
<213> ORGANISM: Unknown Organism
<220> FEATURE:
<223> OTHER INFORMATION: Description of Unknown Organism: Venom derived
      peptide

<400> SEQUENCE: 16

Asp Arg Val Tyr
 1

<210> SEQ ID NO 17
<211> LENGTH: 4
<212> TYPE: PRT
<213> ORGANISM: Unknown Organism
<220> FEATURE:
<223> OTHER INFORMATION: Description of Unknown Organism: Venom derived
      peptide

<400> SEQUENCE: 17

Ile His Pro Phe
 1

<210> SEQ ID NO 18
<211> LENGTH: 8
<212> TYPE: PRT
<213> ORGANISM: Unknown Organism
<220> FEATURE:
<223> OTHER INFORMATION: Description of Unknown Organism: Venom derived
      peptide

<400> SEQUENCE: 18

Asp Arg Val Tyr Ile His Pro Phe
 1               5

FIBRINOGENOLYTIC PROTEASES WITH THROMBOLYTIC AND ANTIHYPERTENSIVE ACTIVITIES: MEDICAL APPLICATION AND NOVEL PROCESS OF EXPRESSION AND PRODUCTION

BACKGROUND OF THE INVENTION

1. Field of the Invention

This invention relates to the purification and use of a novel family of fibrinogenolytic proteases. Specifically, this invention relates to a fibrinogenolytic protease which possesses a strong beta-fibrinogenolytic activity and does not cause formation of fibrin clots, known effects associated with thrombin and thrombin-like proteases of snake venom. In addition, the fibrinogenolytic proteases of the present invention exhibits anti-clotting and antihypertensive effects on experimental animals.

2. Description of the Related Art

Venoms from various snake species alter the haemostatic and blood coagulation systems of human victims or experimental animals in a complex manner. Different venoms contain multiple components which behave as either pro- or anti-coagulants that directly or indirectly induce or inhibit fibrinogen and/or platelet aggregation and related complex biochemical processes, resulting in common clinical complications of blood clotting or uncontrolled hemorrhage by envenomation of snakebites [Ouyang, C. (1957) J. Formosan Med. Assoc. 56, 435–448; Meaume, J. (1966) Toxicon 4, 25–58; and Kini, R. M., and Evans, H. J. (1990) Toxicon 28, 1387–1422.] These apparently contradicting activities have been attributed to the presence of fibrinogenolytic or fibrinogen clotting enzymes in snake venoms [Brinkhous, K. M., and Smith, S. V. (1988) in Hematology, Haemostasis and Animal Venoms (Pirkle, H. and Markland, F. S., Jr., Eds.) Vol. 7, pp. 363–375, Marcel Dekker, New York; Stocker, K. F. (1990) in Medical Use of Snake Venom Proteins (Stocker, K. F., Ed.) pp. 97–160, CRC Press Boston, Mass.; and Tu, A. T. (1982) In Rattlesnake Venoms: Their Actions and Treatment (Tu, A. T., Ed.), pp. 247–312, Marcel Dekker, New York.] On the other hand, platelet-aggregating enzymes in venom generally lack fibrinogenolytic activity, but can directly aggregate platelets in platelet-rich plasma [Serrano, S. M. T., Mentele, R., Sampaio, C. A. M., and Fink, E. (1995) Biochemistry 34, 7186–7193.] Current interest is directed to some fibrinolytic proteinases including metallo-proteinases and thrombin-like enzymes because of their potential clinical application in the treatment of vascular thrombotic diseases [Markland, F. S. Jr. (1998) Thromb. Haemost. 79, 668–674.]

It is well known that snake venoms contain complex mixtures of pharmacologically active peptides and proteins. Reptilian venoms, particularly those obtained from the snake families of Crotalidae and Viperidae, are also shown to possess many different fibrinogenolytic proteases which may initiate or affect blood coagulation process associated with snakebites [Tu, A. T. (1982) In Rattlesnake Venoms: Their Actions and Treatment (Tu, A. T., Ed.), pp. 247–312, Marcel Dekker, New York.] Different researchers reported disparate proteases from venoms of various crotalid snakes. They included crotalase, a thrombin-like enzyme isolated from the American-Eastern diamondback rattlesnake (*Crotalus adamanteus*) [Markland, F. S., and Damus, P. S. (1971) J. Biol. Chem. 246, 6460–6473], hemorrhagic toxins, anticoagulant proteases and kallikrein-like enzymes from the American-Western diamondback rattlesnake *Crotalus atrox* [Pandya, B. V., and Budzynski, A. Z. (1984) Biochemistry 23, 460–470; Bjarnason, J. B., Barish, A., Direnzo, G. S., Campbell, R., and Fox, J. W. (1983) J. Biol. Chem. 258, 12566–12573.] Applicant has previously evaluated the venom components from *Crotalus atrox* and found that all fractions isolated from the anion-exchange chromatography showed varying extents of specific proteolytic activity against alpha-and/or beta-chains of fibrinogen molecules [Chiou, S. -H., Hung, C. -C., and Lin, C. -W. (1992) Biochem. International 26, 105–112; Chiou, S. -H., Hung, C. -C., and Huang, K. -F. (1992) Biochem. Biophys. Res. Commun. 187, 389–396.] Concurrently, studies on the toxin components from Taiwan habu (*Trimeresurus mucrosquamatus*) [Ouyang, C., and Teng, C. M. (1976) Biochim. Biophys. Acta 420, 298–308; Huang, K. -F., Hung, C. -C., and Chiou, S. -H. (1993) Biochem. Mol. Biol. International 31, 1041–1050; and Hung, C. -C., Huang, K. -F., and Chiou, S. -H. (1994) Biochem. Biophys. Res. Commun. 205, 1707–1715.], a major and abundant crotalid species in Taiwan, indicated several kinds of fibrinogenases present in this phylogenetically related species to those American rattlesnakes.

Concerning the pharmacological action of Formosan snake venoms on blood coagulation, it was reported early in 1921–1925 that the crude venoms of two crotalid snake species, *Agkistrodon acutus* and *Trimeresurus gramineus*, had a coagulant action on whole blood and plasma, while the venom of another species *Trimeresurus mucrosquamatus* of the same family showed an inhibitory action Ouyang, C. (1957) J. Formosan Med. Assoc. 56, 435–448. The inhibitory action on blood coagulation was believed to be caused mostly by destruction of fibrinogen in the case of the venom of *Trimeresurus mucrosquamatus*.

As one object of the present invention, applicant discloses herein a family of fibrinogenases isolated from Taiwan habu, which show a specific fibrinogen-degrading activity without being associated with any activity causing fibrin clot formation. In addition, the type of fibrinogenases posesses an unexpectedly strong kallikrein-like hypotensive activity on experimental rats and may find their clinical applications in hypertension therapy.

Another object of the present invention is to develop a new expression process to produce snake venom proteins, including those identified fibrinogenases of the present invention. Expression and purification of recombinant proteins from host organisms are often a critical and time-consuming task in achieving the goal of obtaining pure and large quantities of proteins from recombinant sources [Uhlen, M., and Moks, T. (1990) Methods Enzymol. 185, 129–143.] Facile removal of contaminant expression proteins is essential to accurate characterisation of functional properties of a cloned protein. The most common solution to this problem is to engineer the expressed protein product so as to contain additional amino acid residues which give a unique property to the protein of interest that can be exploited for purification purposes. Such a strategy would greatly increase the availability of recombinant proteins for further structural and functional study. The protein with those additional amino acid residues can generally bind to transition metal ions, thereby allowing the protein to be purified using immobilized metal ion affinity chromatography ("IMAC") [Porath, J., Carlsson, J., Olsson, I., and Belfrage, G. (1975) Nature 258, 598–599.] In this method a specific chelating peptide can be cloned onto the amino terminus ("N-terminus") of a recombinant protein to serve as a purification tag or handle [Smith, M. C., Furman, T. C., Ingolia, T. D., and Pidgeon, C. (1988) J. Biol. Chem. 263, 7211–7215] and subsequently purified by using IMAC.

Recent advance in recombinant DNA technology has allowed in vitro fusion of genes or gene fragments in a simple and predictable manner. There are several reasons to use gene fusion for expression of recombinant proteins in heterologous hosts. In particular, a more reliable and reproducible method to obtain a native protein might be to use in vitro cleavage of the fusion protein, as compared to in vivo removal of the formyl-methionine or cleavage of a signal peptide, which in both cases may yield a heterogeneous N-terminus. Many expression vectors currently used to encode, encoding a protease cleavage site that allows release of carboxyl-terminal ("C-terminal") fusion partners from fusion proteins without leaving unwanted amino-terminal ("N-terminal") amino acid residues behind. In snake venom protein expression system, removal of the upstream fusion partners has been conducted with one of the three different proteases, including thrombin (Maeda, M., Satoh, S., Suzuki, S., Niwa, M., Ioth, N., and Ya-mashina, I. (1991) J. Biochem. (Tokyo) 109, 632–637; Rosenthal, J. A., Levandoski, M. M., Chang, B., Potts, J. F., Shi, Q. -L., and Hawrot, E. (1999) Biochemistry 38, 7847–7855), factor Xa (Rosenthal, J. A., Hsu, S. H., Schneider, D., Gentile, L. N., Messier, N. J., Vaslet, C. A., and Hawrot, E. (1994) J. Biol. Chem. 269, 11178–11185; Zhang, Y., Wisner, A., Maroun, R. C., Choumet, V., Xiong, Y., and Bon, C. (1997) J. Biol. Chem. 272, 20531–20537), and enterokinase (Moura-da-Silva, A. M., Linica, A., Della-Casa, M. S., Kamiguti, A. S., Ho, P. L., Crampton, J. M., and Theakston, R. D. (1999) Arch. Biochem. Biophys. 369, 295–301). However, with a serine protease (Tm-5) from Taiwan habu (*Trimeresurus mucrosquamatus*) (Hung, C. -C., Huang, K. -F., and Chiou, S. -H. (1994) Biochem. Biophys. Res. Commun. 205, 1707–1715), applicants repeatedly encountered difficulties in removing the attached N-terminal polyhistidine tag due to the inability of the commercial enterokinase to cleave efficiently the desired product from the expressed fusion venom protein. There is therefore a need for a different expression system for producing venom proteases.

SUMMARY OF THE INVENTION

These and other objects are attained by the present invention which provides two venom proteases showing a strong kallikrein-like hypotensive activity, potentially useful in hypertension therapy. The present invention also provides a new expression system to produce the aforementioned venom proteases using modern biotechnology.

In the present invention, two serine proteases Tm-VIG and Tm-IIG, isolated and purified from the venom of Taiwan habu, are shown to have strong anti-clotting and hypotensive effects on experimental animals without being associated with any activity that promote formation of fibrin clots. Tm-VIG is so named because its first three N-terminal residues are Val-Ile-Gly while Tm-IIG has Ile-Ile-Gly at the N-terminalus. The isolation and purification are conducted according to applicant's previous disclosure in Biochem. Mol. Biol. Int. 31, 1041–1050 (1993). The content of that publication is incorporated herein by reference in its entirety.

Purified Tm-VIG and Tm-IIG show strong beta-fibrinogenolytic activity, cleaving beta-chain of fibrinogen molecules specifically. They also show strong kallikrein-like activity in vitro, releasing bradykinin from kininogen, but do not coagulate human plasma. Thus, they can decrease fibrinogen levels in plasma and prolong bleeding time without causing formation of fibrin clots, indicating that their specificity is different from thrombin and thrombin-like proteases from snake venoms previously known. Furthermore, these two proteases has a high thermal stability than ancrod and thrombin. In rats, intravenous injection of either of the two proteases has the effect of lowering blood pressure. It is noted that these proteases can cleave angiotensin I and release bradykinin from plasma kininogen in vitro, which is a strong vasodilator and probably responsible for the observed in vivo hypotensive effect.

Thus, the present invention discloses a method of using snake venom to treat hyertension in animals and human subject. Although various snake venom components have been isolated and purified, to applicants' knowledge, no one has taught or suggested the use of a component from snake venom to treat hypertension.

As another object of the present invention, a method of relatively large-scale production of venom proteases useful in hypertension therapy is provided using a protein expression system. Instead of using the conventional enterokinase recognition site, an autocatalytic site is used, based on cleavage specificity of the serine protease, such as TM-VIG and TM-IIG, for post-expression removal of the polyhistidine tag. Genetic engineering is performed so that the autocatalytic site flanks on the 5'-end of the protease gene. Renaturation of the expressed fusion protein showed that the recombinant protease had refolded successfully from the inclusion bodies. Upon autocleavage, the polyhistidine tag with additional amino acid residues appended to the N-terminus of the coding sequence is found to be removed completely. Characterization of the final enzyme produced by the method of the present invention demonstrates that the enzyme is indistinguishable to the one purified from native sources. For example, the recombinant enzyme of the present invention cleaves N-benzoyl-Pro-Phe-Arg-p-nitroanilide, a unique and strict substrate for native Tm proteases reported previously.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

FIG. 1. N-terminal extension sequences of various gene constructs and their corresponding amino acid sequences. They are composed of the N-terminal coding sequence for the venom protease (underlined), the recognition site of enterokinase or the autolytic sites of Tm-VIG (boldface), and BamHI site (italicized) plus an initiating sequence (MRGS) from the expression vector. The dashed lines indicate identical sequence segments to those of sequences 1 and 2. N-terminal extension sequences 1 to 6 are herein identified as SEQ ID 1 to 6.

DETAILED DESCRIPTION OF THE PRESENTLY PREFERRED EMBODIMENTS

Expression and purification of Tm-5 protease is outlined below and further detailed in S. H. Chiou et al., Biochemical and Biophysical Research and Communications 275, 924–930 (2000), the contents of which is incorporated by reference.

Gene Fusion Systems Used to Facilitate Protein Purification.

We have adopted the strategy of Smith, M. C., Furman, T. C., Ingolia, T. D., and Pidgeon, C. (1988) J. Biol. Chem. 263, 7211–7215 of attaching an N-terminal polyhistidine tag to facilitate the affinity purification using immobilized metal ion affinity chromatography (IMAC) [Porath, J., Carlsson, J., Olsson, I., and Belfrage, G. (1975) Na-ture 258, 598–599.] However, in the final stage of removing the poly-histidine tag plus an N-terminal extension of pentapeptide (Asp)4-Lys by site-specific enterokinase, difficulties often arise due to the inability of obtaining clean cleavage of the attached affinity tag by the enzyme. In order to circumvent the difficulty encountered in the expression and purification of the recombinant products in E. coli system, we have developed a novel strategy to facilitate the removal of attached tags. For the expression and refolding of recombinant Tm-5 (rTm-5) in bacteria we made a synthetic fusion construct in E. coli expression vector pQE30, which contained the coding region for initiation translation peptide (Met-Arg-Gly-Ser), followed by a polyhistidine tag with a stretch of six histidines, a protease recognition site for an N-terminal extension of pentapeptide (Asp)4-Lys or an N-terminal extension of tripeptides (FIG. 1) designed for autolytic cleavage by the expressed protease, and ending with a sequence coding for rTm-5.

Expression and Purification of Recombinant Tm-5 Protease.

Figure 2:
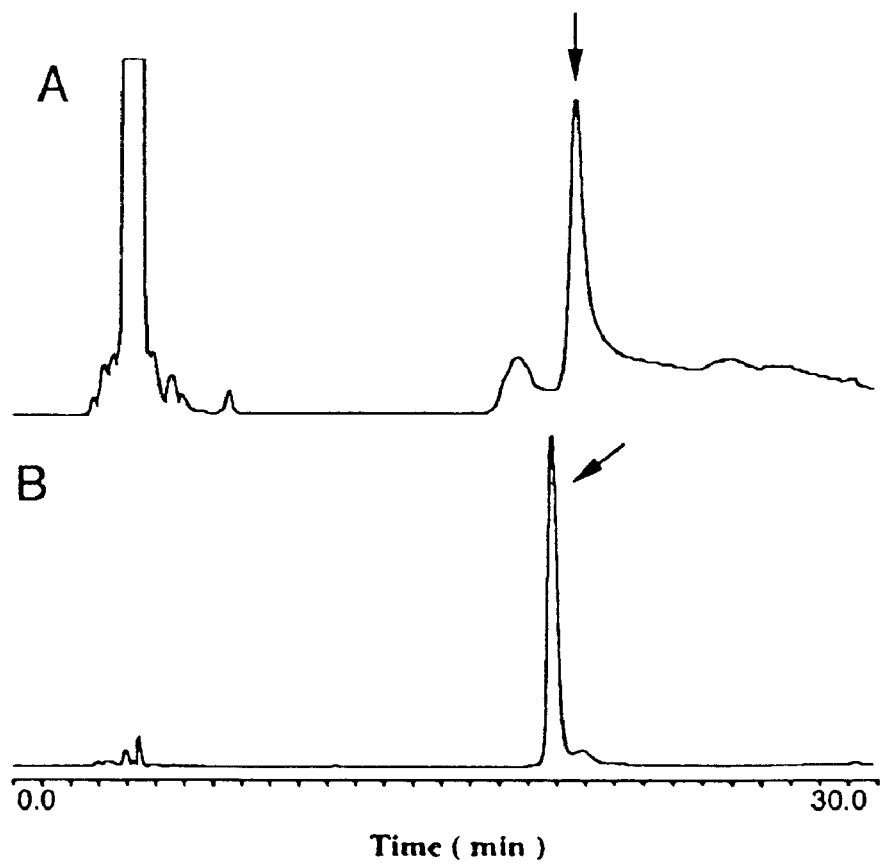
FIG. 2. Purification of recombinant Tm-5 with histidine tag and tripeptide (Phe-Leu-Arg) extension by reversed-phase HPLC. The unfolded and refolded recombinant proteins isolated from His-tagged affinity resin were applied to a reversed-phase C4 column. The HPLC was run in a linear gradient of 10–75% solvent B (95% acetonitrile containing 0.1% trifluoroacetic acid (TFA)) with 5% acetonitrile/0.1% TFA (solvent A) as the starting and equilibration eluent. The flow rate of column eluates was set at 1 ml/min and monitored at UV 280 nm. Arrows indicate the unfolded rTm-5 (A) and refolded rTm-5 (B) proteases.
Figure 3:
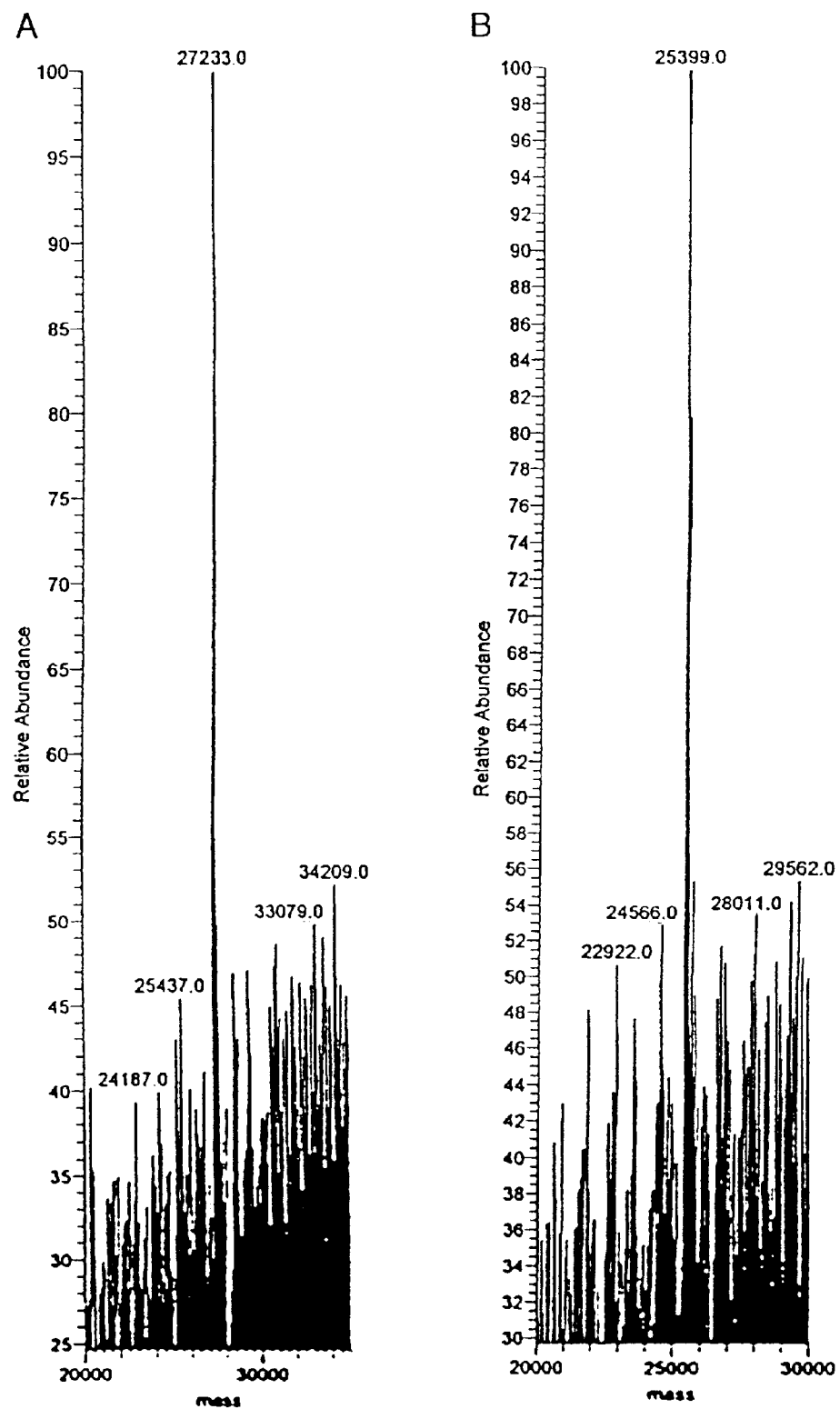
FIG. 3. The mass spectra of recombinant Tm-5 proteases as determined by electrospray ionization mass spectrometry. The molecular ions of unfolded (A) and refolded (B) from HPLC were detected with masses of 27233 and 25399 Da.

The recombinant Tm-5 fusion protein was overexpressed in E. coli upon induction with IPTG. The expressed product was generated in a form of inclusion body with limited solubility. The polyhistidine tag facilitated purification of the rTm-5 fusion protein from the cell lysate in denaturation buffer containing 8 M urea by immobilized nickel ion affinity chromatography (IMAC, NiNTA resin). The refolding at the stage with fusion protein containing the polyhistidine tag followed by autolytic release of rTm-5 by the expressed protease was found to be more efficient than the original protocol of refolding the released product of rTm-5 polypeptide from the fusion protein cleaved by enterokinase (Rosenthal, J. A., Hsu, S. H., Schneider, D., Gentile, L. N., Mess-ier, N. J., Vaslet, C. A., and Hawrot, E. (1994) J. Biol. Chem. 269, 11178–11185). In addition, we have also found that enterokinase can degrade unfolded polypeptide randomly before refolding (data not shown). The denatured and unfolded rTm-5 eluted from the NiNTA resin was then injected onto a C4 column. The elution profile (FIG. 2) showed that the unfolded rTm-5 was eluted later in the gradient than the refolded rTm-5. The eluted samples purified from HPLC were then analyzed by ESI-MS. The unfolded and refolded proteases were detected with masses of 27233 and 25399 Da, respectively (FIG. 3). The result clearly indicated that the fusion partner (an estimated mass of 1832 Da), including the His-tag appended to the N-terminus of the rTm-5 sequence, had been removed successfully.

Immunoblot Analysis of Recombinant Tm-5 Protease.

Figure 4:
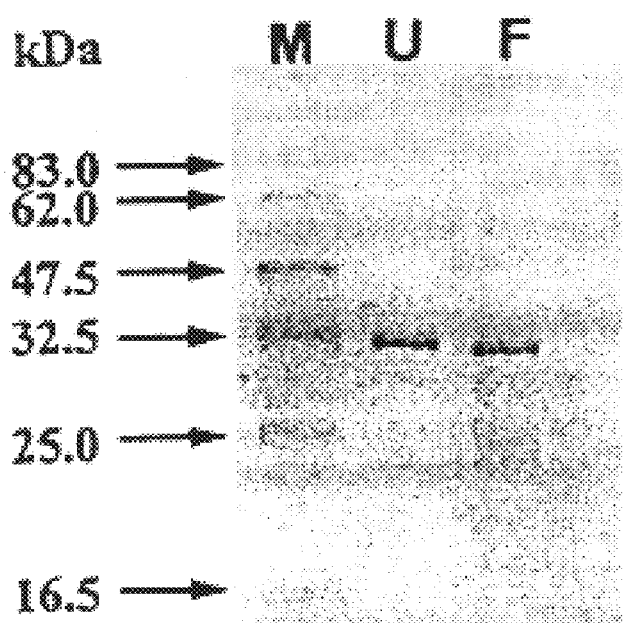
FIG. 4. Immunoblot screening of expressed recombinant venom proteases. The gels were subjected to electroblotting onto a nitrocellulose membrane after SDS-PAGE followed by immunological analysis using rabbit polyclonal antibody against native Tm-VIG. Lane M, prestained standard protein markers, with 6 arrows on the left side showing the positions of markers; lane U, unfolded recombinant Tm-5; lane F, refolded recombinant Tm-5.

The predicted molecular mass of the mature Tm-VIG is about 25 kDa based on the deduced protein sequences of cDNA clones, which is lower than 30 kDa estimated by SDS-gel electrophoresis under reducing conditions. It is noteworthy that molecular-weight estimations by SDS-PAGE were slightly different between two forms. However, both the unfolded and refolded rTm-5 proteases can cross-react with a polyclonal rabbit anti-Tm-VIG antibody by using immunoblot analysis (FIG. 4).

N-terminal Sequence Analysis.

N-terminal sequence analysis of various refolded rTm-5 proteases with different N-terminal extension peptides corroborated that these proteases had removed histidine-tagged fusion peptides by autolytic cleavage from recombinant rTm-5 fusion proteins (Table 1). All designed N-terminal extension peptides were cleaved to yield the correct N-termini (VIGGDE) for this refolded recombinant protease except fusion proteins containing Pro-Phe-Arg and Leu-Phe-Arg extension peptides, which produced one extra N-terminus due to unexpected double cleavages by the expressed protease.

Substrate Specificity of Expressed Recombinant Tm-5 Proteases.

Figure 5:
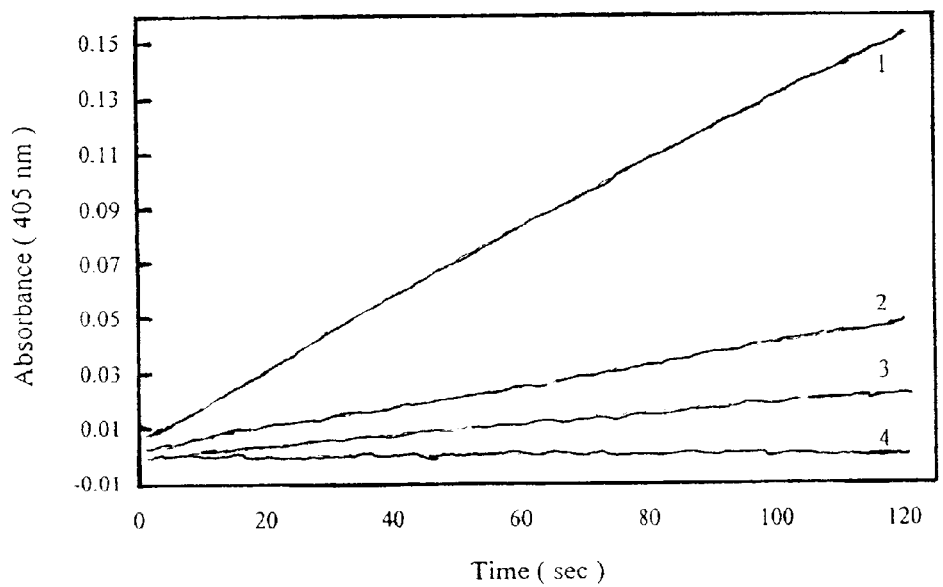
FIG. 5. Enzyme activity assays of recombinant Tm-5 on synthetic substrates. Activity was measured by using chromogenic substrates for rTm-5. Line 1, 0.1 mM N-benzoyl-Pro-Phe-Arg-pNA and 0.2 μg (0.1 nM) enzyme; line 2, 0.3 mM N-BENZOYL-PHE-VAL-ARG-PNA and 0.4 μg enzyme (0.2 nM); line 3, 0.3 mM N-p-tosyl-Gly-Pro-Arg-pNA and 0.4 μg enzyme (0.2 nM); line 4, 0.3 mM N-p-tosyl-Gly-Pro-Lys-pNA and 0.4 μg enzyme (0.2 nM). Proteolytic activities using chromogenic substrates were measured on a spectrophotometer at 405 nm.

In previous studies of activity assays for expressed proteases, we found that expressed products with intact histidine-tag and the attached pentapeptide possessed similar proteolytic activity to that of the native Tm-VIG enzyme using chromogenic substrates (data not shown). In this study, expressed recombinant proteases with removal of attached fusion peptides by autolysis were found to show similar activity to native venom proteases, both groups cleaving efficiently p-nitroanilide from several synthetic peptide substrates. As shown in FIG. 5, N-benzoyl-Pro-Phe-Arg p-nitroanilide, a specific substrate for kallikrein, was most susceptible to hydrolysis by rTm-5 (line 1 of FIG. 5). However, D-Val-Leu-Lys p-nitroanilide which is a substrate for plasmin was shown to be a poor substrate for rTm-5 (line 4 of FIG. 5). Enzyme activity assays of refolded recombinant protease rTm-5 using N-benzoyl-Phe-Val-Arg-pNA and N-p-tosyl-Gly-Pro-Arg-pNA (lines 2 and 3 of FIG. 5), both being substrates of thrombin, exhibit intermediate activity.

To our knowledge this is the first disclosed design of nonconventional extension peptides coupled with autolysis of a specific venom protease to obtain a functional recombinant product free of histidine-tag and fusion peptides.

Materials and Methods

Materials. The synthetic substrates were from Sigma Chemical Co. (St. Louis, Mo.). Restriction endonucleases, pfu polymerase and isopropyl-β-D-thiogalactoside (IPTG) were obtained from Promega (Promega Corp., Madison, Wis.). Antibodies directed against kallikrein-like fibrinogenolytic enzymes were purified from a rabbit antiserum, obtained by immunization with Tm-VIG from Taiwan habu (Hung, C. -C., Huang, K. -F., and Chiou, S. -H. (1994) Biochem. Biophys. Res. Commun. 205, 1707–1715).

Construction of recombinant Tm-5 expression plasmids. Polymerase chain reaction was employed to construct a recombinant protease corresponding to Tm-5 clone. Oligonucleotide A, a 39-mer (5'-GCGGATCCGATGACGATGA-CAAAGTCATTGGAGGTGATG)for Tm-5 clone containing the enterokinase recognition site (boldface) and oligonucleotide B, a 33-mer (5'-GCGGATCCXXXXXXXXX-GTCATTGGAGGTGATG) for Tm-5 clone containing the autolytic recognition site (boldface XX-) were synthesized. They both include the N-terminal coding sequence (underlined), and BamHI site (italicized).

Oligonucleotide C, a 26-mer (5'-GCCTGCAGTCA CAGGGGGCAGGTTAC) was complementarily overlapped with the C-terminal end of Tm-5, which contained the PstI site (italicized) linked to the translational stop codon (boldface) at the C-terminal end of the coding region (underlined).

Expression and purification of recombinant Tm-5 protease. A nucleotide segment coding for one of the Tm proteases (Tm-5) was synthesized by amplifying Tm-fibrinogenase open reading frame of the cDNA clone Tm5 using two primers designed for introducing cleavage sites for BamHI and PstI plus a 6×His tag and an N-terminal extension of pentapeptide (Asp)4-Lys, or an N-terminal extension of tripeptides designed for autolytic cleavage by the expressed protease. This PCR-synthesized nucleotide segment was cloned in-frame into the BamHI/PstI sites of the *E. coli* expression vector pQE30 (Qiagen GmbH, Hilden, Germany). The deduced expressed N-terminal sequences are shown in FIG. 1. Recombinant plasmids were identified by BamHI/PstI analysis and clones containing the correctly sized insert were sequenced. For induction of gene expression, *E. coli* M15 cells containing recombinant plasmids were grown at 37° C. in one liter of LB medium containing 25 μg/ml kanamycin and 100 μg/ml ampicillin. When the A600 nm of the growing culture reached 0.7, IPTG was added to a final concentration of 2 mM. The culture was induced for a period of up to 4 h.

Purification of histidine-tagged recombinant Tm-5 protease. Culture containing IPTG-induced cells (1000 ml) was centrifuged and the pellet was resuspended (5 ml per gram) in denaturation buffer (8 M urea, 0.5 M NaCl, 0.02 M Tris/HCl, pH 8.0). The lysed cells were stirred for 1 h at room temperature. The suspension was then centrifuged at 10,000 g for 15 min at 4° C. The supernatant of centrifuged lysate was then loaded onto a 4 ml nickel nitrilotriacetic acid (NiNTA) resin packed column (Qiagen GmbH) preequilibrated with denaturation buffer and washed with washing buffer (40 mM imidazole in denaturation buffer) followed by elution buffer (1 M imidazole in denaturation buffer). The desired fusion proteins were analyzed by SDS-PAGE and Western blot analysis.

Immunoblot Analysis of the Expressed Recombinant Protease.

SDS-polyacrylamide slab gel (5% stacking/15% resolving gel) electrophoresis (SDS-PAGE)) was routinely carried out as described (Laemmli, U. K. (1970) Nature 227, 680–685). For immunoblot screening of expressed Tm-5 protease, the gel was subjected to electroblotting onto a nitrocellulose membrane after SDS-PAGE followed by using a polyclonal rabbit anti-Tm-VIG antibody (Hung, C. -C., Huang, K. -F., and Chiou, S. -H. (1994) Biochem. Biophys. Res. Commun. 205, 1707–1715) as primary antibody and reacted with peroxidase-conjugated goat anti-rabbit IgG+IgM (H+L) (Jackson Immuno-Research Laboratories, West Grove, Pa.). A color development reaction was carried out using diaminobenzidine and hydrogen peroxide.

Characterization of recombinant Tm-5 protease. The His-tagged Tm-fusion protein eluted from Ni-NTA resin was diluted with 50 mM Tris, pH 8.0, buffer containing 5 mM cysteine-HCl to a final protein concentration of 0.01–0.05 mg/ml. The refolding process was allowed to proceed at room temperature and was monitored by assaying the amidolytic activity of recombinant Tm-5 on chromogenic substrate N-benzoyl-Pro-Phe-Arg-pNA. The refolded fusion protein was concentrated in an Amicon cell concentrator with constant stirring under nitrogen pressure and purified further on a Sephadex-G 75 (Pharmacia, Uppsala, Sweden) column, peaks with activity were collected and purified by FPLC (fast performance liquid chromatography) in a Mono Q (HR 5/5) column with Amersham/Pharmacia Biotech equipment (Pharmacia, Uppsala, Sweden). Eluted proteins purified from the last step were treated (i) with enterokinase in 50 mM Tris, pH 7.5 to remove His-tag and N-terminal extension of pentapeptide (Asp)4-Lys, or (ii) without enterokinase, i.e., autolytic cleavage of histidine tag and the attached N-terminal extension tripeptides by the expressed protease. The concentration of Tm-5 venom protease was determined by the Bio-Rad protein assay kit.

Chromogenic assays. The enzyme activity of expressed venom proteases was determined by using chromogenic substrates. The amidolytic activity towards the chromogenic substrates was measured with a Ultrospec 4000 spectrophotometer (Amersham/Pharmacia) in a plastic cuvette with 1-cm path length. Assays were performed in 50 mM Tris-HCl, pH 8.0, in a total volume of 750 $\mu$l at 37° C. The final concentration of enzymes varied from 1.0 to 2.0 nM and that of the chromogenic substrates from 0.1 to 0.3 mM. The formation of p-nitroaniline was monitored at 405 nm as a function of time.

N-terminal amino acid sequence analyses. The unfolded or re-folded recombinant Tm-5 protease purified from His-tagged affinity resin was applied to a reversed-phase HPLC (Vydac C4 column, 4.6×250 mm). The HPLC was run in a linear gradient of 10–75% solvent B (95% acetonitrile containing 0.1% trifluoroacetic acid (TFA)) with 5% acetonitrile/0.1% TFA (solvent A) as the starting and equilibration eluent. The flow rate of column eluates was set at 1 ml/min and monitored at UV 280 nm. Peak fractions were collected and lyophilized. N-terminal sequence analysis was carried out by automated Edman degradation with a microsequencing sequencer (Model 477A, Applied Biosystems).

Molecular mass analyses. Expressed Tm-5 recombinant protease was dissolved in 50% acetonitrile containing 1% acetic acid to make a final concentration of 0.1 $\mu$M. The sample was then analyzed in an LCQ mass spectrometer (Finnigan, San Jose, Calif.) at an infusion rate of 5 $\mu$l/min. The spectra were analyzed with a software (LCQ Bio-Works) from the manufacturer.

While the above purification method has been described for the Tm-VIG enzyme, the purification method can be used to obtained other venom proteases including but not limited to Tm-IIG. We have found that purified venom proteases from *Trimeresurus mucrosquamatus,* denoted Tm, have fibrinogenolytic activity making them useful as anti-clotting agents. Additionally, we have found that purified venom proteases from Tm also exhibit hypotensive effects. The following outlines the characterization of these activities, and is reported in S. H. Chiou et al., Biochemical and Biophysical Research Communications 281, 1012–1018 (2001), the contents of which is herein incorporated by reference.

Figure 6:
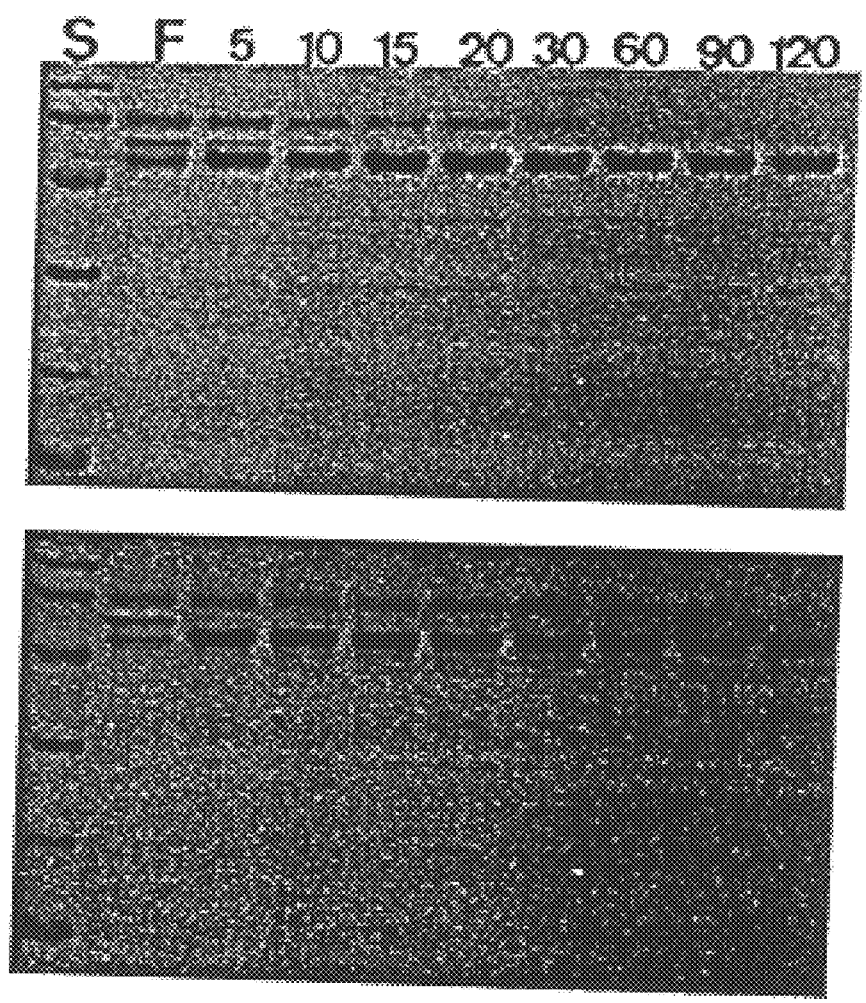
FIG. 6. Time-course study of fibrinogenolytic activity of purified proteases (Tm-VIG and Tm-IIG) on SDS-PAGE. Lane F, purified fibrinogen in the absence of proteases, the three subunit chains are α, β, and γ chains of fibrinogen respectively from the top end downwards; Lane S, standard molecular mass markers (in kDa): phosphorylase b (94), bovine serum albumin (66), ovalbumin (45), carbonic anhydrase (30), soybean trypsin inhibitor (20), and α-lactalbumin (14). Lanes with indicated numbers 5–120 denote time-course digestion of fibrinogen with purified proteases Tm-VIG (top) and Tm-IIG (bottom) at 37 C for 5, 10, 15, 20, 30, 60, 90 and 120 min, respectively. Note that the proteases show specific cleavages first on β and then α chains with γ chain relatively resistant to digestion.

Fibrinogenolytic activity and substrate specificity of Tm-VIG and Tm-IIG. Both groups of fibrinogenolytic enzymes, i.e., Tm-VIG and Tm-IIG hydrolyzed $\beta$ chain of fibrinogen within 5 min with relatively lower activity on $\alpha$ chain while $\gamma$ chains remained intact even at the end of 120 min (FIG. 6). Tm-VIG and Tm-IIG can also cleave p-nitroaniline from several synthetic colored peptide substrates. N-benzoyl-Pro-Phe-Arg p-nitroanilide, a specific synthetic substrate for kallikrein-like proteases was most susceptible to hydrolysis by Tm-VIG and Tm-IIG. They also showed relatively high activities towards N-p-tosyl-arginine methyl ester (TAME), indicating that both groups are members of serine proteases family. However D-Val-Leu-Lys p-nitroanilide which is a specific substrate for plasmin was demonstrated to be a very poor substrate for these two types of fibrinogenases (unpublished results), attesting to some distinct features of these fibrinogen-digesting proteases as compared with conventional serine proteases involved in the process of blood coagulation.

Figure 7:
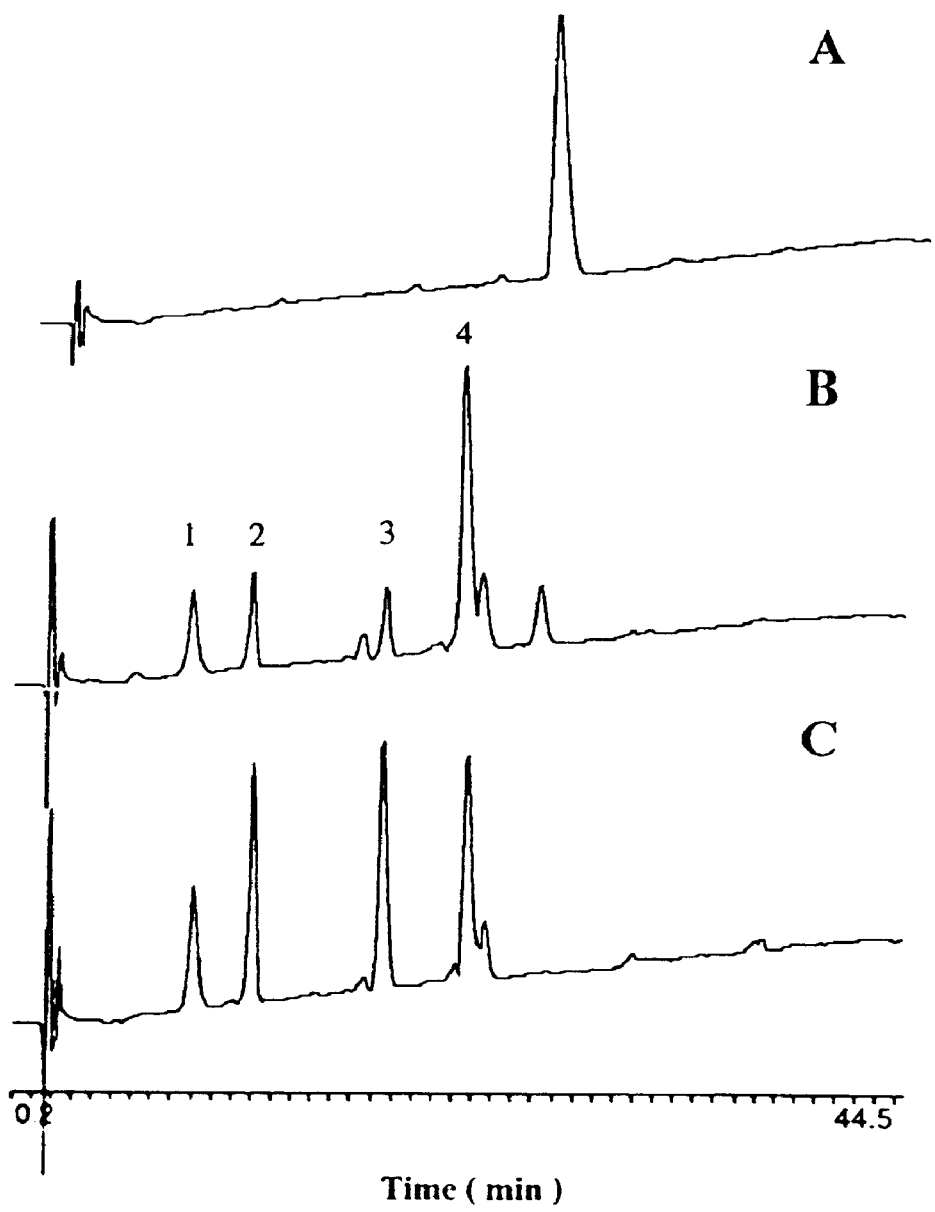
FIG. 7. HPLC chromatograms of angiotensin I cleavage induced by Tm-VIG and Tm-IIG. Chromatography was analyzed by HPLC (Bio-Rad Bio-Sil ODS-5S $C_{18}$ column, 4×250 mm). The HPLC was run for 35 min in a linear gradient of 0–75% solvent B (95% acetonitrile containing 0.1% trifluoroacetic acid (TFA)) with 5% acetonitrile/0.1% TFA (solvent A) as the starting and equilibration eluent. The flow rate of column eluates was set at 1 ml/min. Each chromatogram represents angiotensin I alone (A) and angiotensin I digested with Tm-VIG (B) or Tm-IIG (C). The labeled peaks indicate 4 major proteolytic fragments by digestion.
Figure 8:
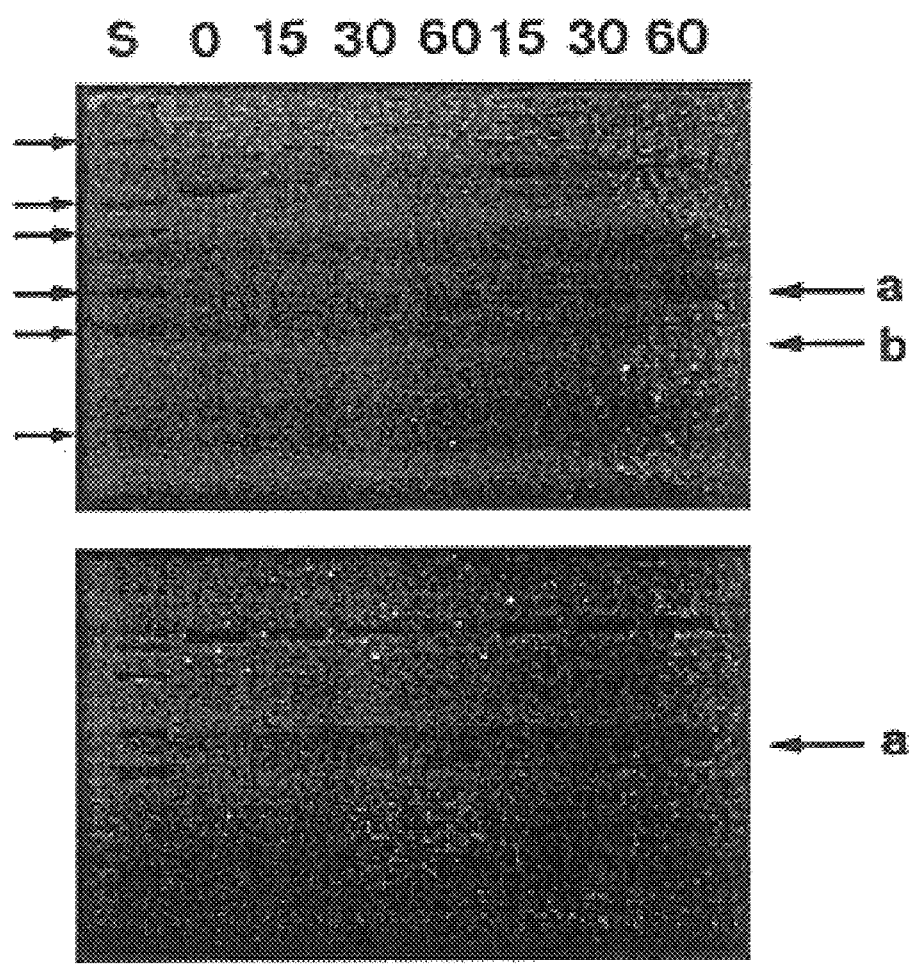
FIG. 8. Time-course study of kallikrein-like activity of venom proteases on SDS-PAGE. High molecular-weight kininogen (114 kDa) was incubated with plasma kallikrein or Tm-VIG (Top, left to right), and Tm-IIG or Ancrod (Bottom, left to right) at 37 C for 15, 30, and 60 min, respectively. Arrows a and b indicate a 58 kDa light-chain fragment and a 45 kDa modified light-chain fragment formed after cleavage with plasma kallikrein. Lane S, standard high-molecular-mass markers (in kDa): myosin (212), β-galactosidase (116), phosphorylase b (94), bovine serum albumin (66), catalase (57), and aldolase (40).

Incubation of angiotensin I with these two venom proteases resulted in similar degradation patterns. The four major peptide fragments released by specific cleavage on angiotensin I with Tm-VIG and Tm-IIG as determined from amino acid compositions of these peptide fragments are as follows: His-Leu, Asp-Arg-Val-Tyr, Ile-His-Pro-Phe, and Asp-Arg-Val-Tyr-Ile-His-Pro-Phe (corresponding to four major peptide peaks in FIG. 7). This would indicate that these two proteases act on the same sites in angiotensin I. In addition, when kininogen was incubated with purified Tm-VIG or Tm-IIG, the disappearance of kininogen coupled with the formation of the major degradation protein fragment of 58 kDa chain is very similar to that observed for human kallikrein (FIG. 8). The kinin released by Tm-VIG and Tm-IIG from kininogen was further identified by reverse-phase HPLC. Comparison of the fragmentation profiles by mass spectroscopy using synthetic bradykinin as a marker standard identified one of the released peptides as bradykinin (data not shown), pointing to the fact that these two venom proteases may possess genuine hypotensive effect in vivo through bradykinin.

Figure 9:
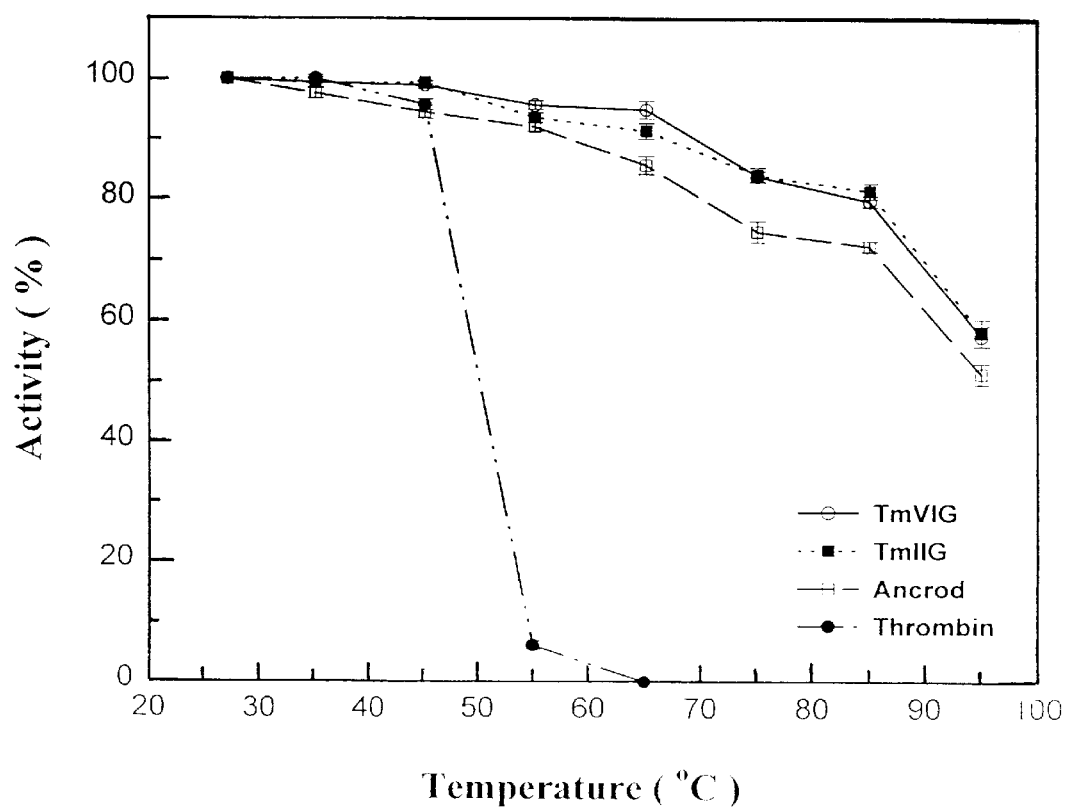
FIG. 9. Effect of temperature on the activity of purified fibrinogenolytic proteases, ancrod and human thrombin. Activity was measured by using 0.1 mM N-benzoyl-Pro-Phe-Arg p-nitroanilide as substrate for Tm-VIG and Tm-IIG, and 0.1 mM N-p-tosyl-Gly-Pro-Arg p-nitroanilide for ancrod and thrombin due to different substrate specificities among these proteases. Percent activity at different temperatures with reference to that at the ambient room temperature (100%) was compared for these four proteases. The proteolytic activities using synthetic chromogenic substrates were measured on a spectrophotometer at 405 nm. Data are presented as mean SEM (n=3).

Stability of purified venom proteases with beta-fibrinogenolytic activity. We have carried out thermal stability analysis of Tm-VIG and Tm-IIG by incubating these proteases at different temperatures for 30 min and examined the fibrinogenolytic activity after heating. It is of surprise to find that these proteases similar to another snake venom protease (ancrod) [Burkhart, W., Smith, G. F. H., Su, J. L., Parikh, I., and LeVine III, H. (1992) FEBS Lett. 297, 297–301; Au, L. C., Lin, S. B., Chou, J. S., Teh, G. W., Chang, K. J., and Shih, C. M. (1993) Biochem. J. 294, 387–390] isolated from Malayan pit viper *Calloselasma rhodostoma* were heat-stable to about 95 C. They still maintained their activity at a level of 50–65% activity even after 30 min heating at this high temperature whereas human thrombin lost activity completely at about 65 C (FIG. 9). Both proteases are also more stable than various fibrinogenases previously identified from American rattlesnake venoms [Chiou, S. -H., Hung, C. -C., and Lin, C. -W. (1992) Biochem. International 26, 105–112; Chiou, S. -H., Hung, C. -C., and Huang, K. -F. (1992) Biochem. Biophys. Res. Commun. 187, 389–396], which are also stable only to about 60–65 C.

Figure 10:
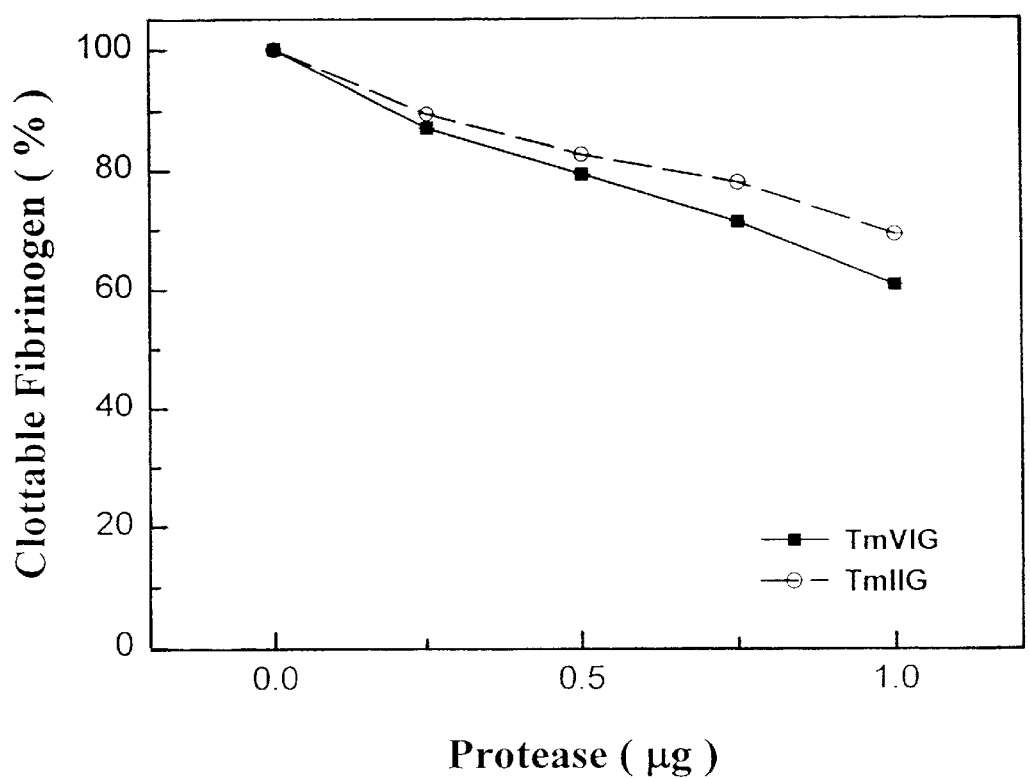
FIG. 10. Effect of kallikrein-like Tm proteases on apparent fibrinogen concentration in plasma measured with a coagulometer. The samples from human Control Plasma N were mixed with various concentrations of venom proteases. Values are given as percent of original fibrinogen concentration measured in the absence or presence of venom proteases using the Control Plasma N solution without protease as reference. Data are assayed in triplicate measurements.
Figure 11:
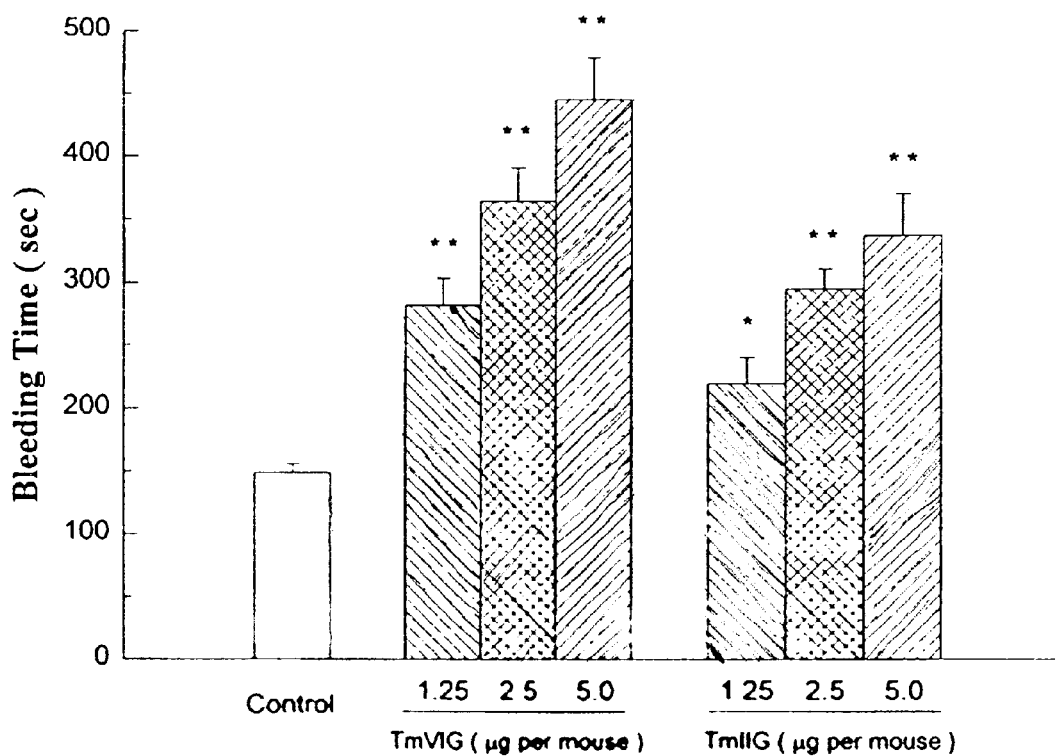
FIG. 11. Effect of kallikrein-like Tm proteases on tail bleeding time in mice by a filter paper method. Bleeding time was measured 5 min after the intravenous administration of saline or various doses of proteases. Data are presented as mean SEM (n=6), with significance levels at *P<0.05 or **P<0.01 as compared with the control.

Effects of proteases on total clottable fibrinogen and bleeding time. The conversion of fibrinogen into fibrin plays an important role in coagulation and hemostasis. The final and most defined function of blood coagulation is its effect on plasma clottability. Thus the measurement of clottable fibrinogen in plasma has become a standard protocol for comparison of effects of various biological factors or pharmaceutical agents on the blood clotting process [Gaffney, P. J., and Wong, M. Y. (1992) Thromb. Haemostasis 68, 428–432.] We have used the clotting-time measurement to determine clottable fibrinogen in plasma after treating with Tm proteases. Both venom proteases could prolong clotting times by degrading plasma fibrinogens directly. Total clottable fibrinogen levels were decreased after incubation with purified Tm-VIG/Tm-IIG for 2 min (FIG. 10). However, the blood clotting cannot be induced and clotting-times lengthened indefinitely when the concentrations of proteases were higher than 1 μg, corroborating the strong fibrinogenolytic activity associated with these two novel venom proteases. The bleeding times measured after surgical transections on tails upon intravenous administration of proteases to mice were significantly prolonged in a dose-dependent manner (FIG. 11). It is noteworthy that the anti-clotting or bleeding effect of Tm-VIG was significantly stronger than that of Tm-IIG. Similar to clottable fibrinogen assays, the bleeding times were found to lengthen to more than 10 min and hemorrhagic side-effects appeared when amounts of proteases injection were higher than 5 μg per mouse. Therefore from the in vitro clottable fibrinogen assays and in vivo bleeding time measurements, it is conceivable that Tm-VIG and Tm-IIG may be directly involved in decreasing the levels of fibrinogen in the plasma through defibrinogenation.

Figure 12:
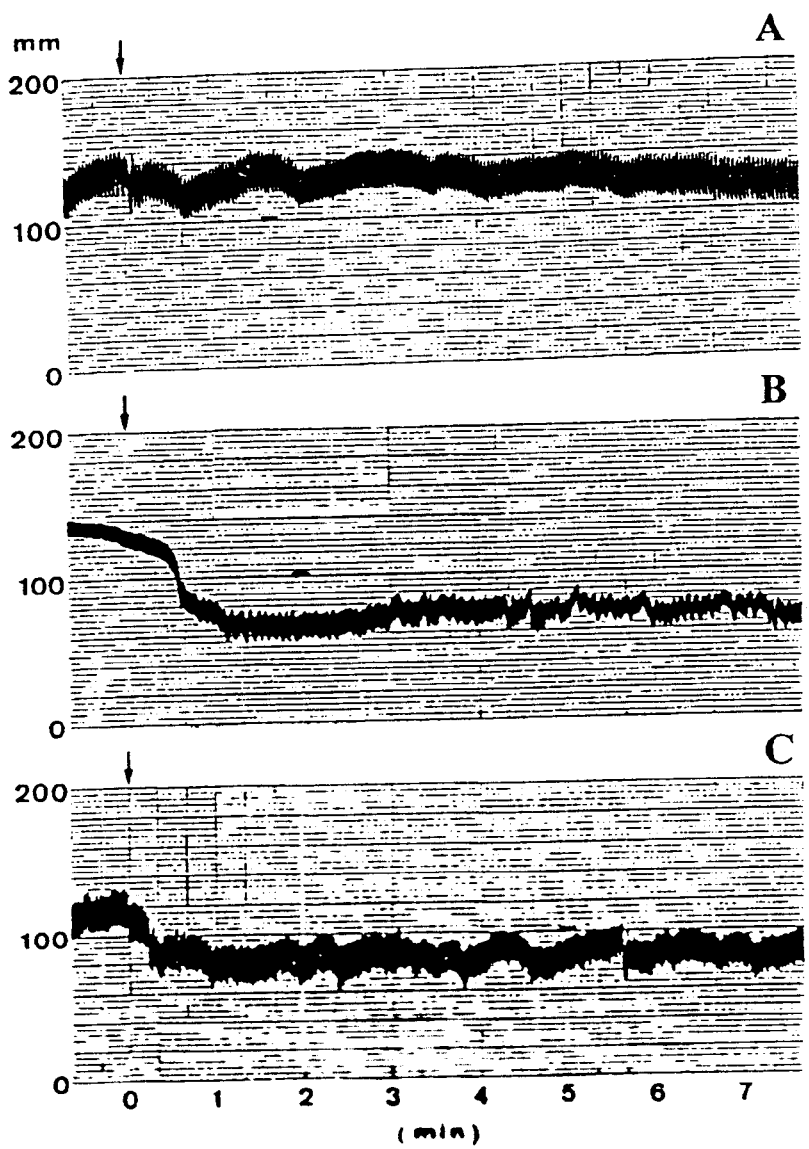
FIG. 12. Hypotensive effect on rat blood pressure of kallikrein-like Tm fibrinogenases from Taiwan habu. (A) Blood pressure change after intravenous (i.v.) injection with normal saline; (B) Blood pressure change after i.v. injection of Tm-VIG (0.5 μg/g weight); (C) Blood pressure change after i.v. injection of Tm-IIG (0.5 μg/g weight). Arrows indicate starting points for sample injections. Note that Tm-IIG seemed to show a lower hypotensive activity than Tm-VIG under similar experimental conditions.

Hypotensive effects of Tm proteases on experimental rats. The hypotensive effects of proteases on rat blood pressure were investigated by injecting these proteins into cannulated rats. A significant blood pressure drop was observed with Tm-VIG injection (FIG. 12). Injection of Tm-IIG showed a milder effect. The hypotensive effect exhibited by these venom proteases is likely due to their inherent kallikrein-like activity. There is a possibility that Tm-VIG and Tm-IIG may directly affect the blood coagulation pathway by specifically cleaving beta chains of animal fibrinogens and act like plasma kallikreins to cleave kininogen. This kallikrein-like activity is especially intriguing since the reported alpha-fibrinogenases like ancrod did not show such a high specificity against kininogen (data not shown). Moreover both Tm-VIG and Tm-IIG demonstrated no obvious ability to induce or inhibit platelet aggregation, in great contrast with some venom antithrombotic factors reported in the literature.

All references cited herein are incorporated by reference.

TABLE 1

Comparison of the Constructed N-Terminal Extension Peptide Sequences and N-Terminal Sequences Determined for Refolded Proteases

| Constructed Tm-5 sequences | N-terminal sequences of refolded Tm-5 |
| --- | --- |
| -FLRVIGGDE- | VIGGD |
| -FVRVIGGDE- | VIGGD |
| -FPRVIGGDE- | VIGGD |
| -PFRVIGGDE- | RVIGGD |
|  | VIGGD |
| -LFRVIGGDE- | RVIGGD |
|  | VIGGD |

I claim:

1. A method of treating a cardiovascular disorder selected from the group consisting of hypertension, stroke and thrombosis in an animal in need thereof, comprising administering an effective amount of purified protease Tm-VIG.

2. The method of claim 1 wherein the cardiovascular disorder is hypertension.

3. The method of claim 1 wherein the cardiovascular disorder is a stroke.

4. The method of claim 1 wherein the cardiovascular disorder is thrombosis.

5. The method of claim 1, wherein the purified protease is capable of cleaving angiotensin I.

6. The method of claim 1, wherein the purified protease is capable of releasing bradykinin from plasma kininogen.

7. The method of claim 1, wherein the purified protease is capable of digesting N-benzoyl-Pro-Phe-Arg-p-nitroanilide.

* * * * *